(12) United States Patent
Gurm

(10) Patent No.: US 8,267,953 B2
(45) Date of Patent: Sep. 18, 2012

(54) ANGIOPLASTY BALLOON WITH THERAPEUTIC/ASPIRATION CHANNEL

(75) Inventor: Hitinder Gurm, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 12/983,656

(22) Filed: Jan. 3, 2011

(65) Prior Publication Data

US 2011/0098798 A1 Apr. 28, 2011

Related U.S. Application Data

(63) Continuation of application No. 11/935,131, filed on Nov. 5, 2007, now Pat. No. 7,862,576.

(60) Provisional application No. 60/857,082, filed on Nov. 6, 2006.

(51) Int. Cl.
*A61M 29/00* (2006.01)

(52) U.S. Cl. .................. 606/194; 604/102.01; 604/131

(58) Field of Classification Search ............. 604/19, 604/95.01–95.05, 96.01–103.04, 523–532; 606/194

See application file for complete search history.

(56) References Cited

U.S. PATENT DOCUMENTS

| | | | |
|---|---|---|---|
| 4,292,976 A | 10/1981 | Banka | |
| 4,299,226 A | 11/1981 | Banka | |
| 5,279,562 A * | 1/1994 | Sirhan et al. | 604/103.09 |
| 5,409,495 A * | 4/1995 | Osborn | 623/1.11 |
| 5,776,142 A | 7/1998 | Gunderson | |
| 5,951,586 A | 9/1999 | Berg et al. | |
| 6,041,252 A | 3/2000 | Walker et al. | |
| 6,139,524 A | 10/2000 | Killion | |
| 6,142,926 A * | 11/2000 | Schneiderman | 600/3 |
| 6,261,273 B1 | 7/2001 | Ruiz | |
| 6,379,378 B1 | 4/2002 | Werneth et al. | |
| 6,440,097 B1 | 8/2002 | Kupiecki | |
| 6,540,734 B1 | 4/2003 | Chiu et al. | |
| 6,575,993 B1 * | 6/2003 | Yock | 606/194 |
| 6,576,001 B2 | 6/2003 | Werneth et al. | |
| 6,709,427 B1 | 3/2004 | Nash et al. | |
| 6,716,190 B1 | 4/2004 | Glines et al. | |
| 6,730,119 B1 | 5/2004 | Smalling | |
| 6,749,628 B1 | 6/2004 | Callol et al. | |
| 6,767,345 B2 | 7/2004 | St. Germain et al. | |
| 6,872,192 B2 | 3/2005 | Nash et al. | |
| 6,918,869 B2 | 7/2005 | Shaw et al. | |
| 6,966,889 B2 | 11/2005 | Saab | |
| 6,989,024 B2 | 1/2006 | Hebert et al. | |

(Continued)

OTHER PUBLICATIONS

Murakami et al., "CT arterial portography and CT arteriography with a triple-lumen balloon catheter," Acta Radiol 38(4 Pt 1):553-7 (1997).

*Primary Examiner* — Christopher D Koharski
*Assistant Examiner* — Gerald Landry, II
(74) *Attorney, Agent, or Firm* — Marshall, Gerstein & Borun LLP

(57) ABSTRACT

An angioplasty balloon catheter with an added channel for delivering medication or removing body fluids distal to the site of angioplasty is disclosed. The balloons are especially useful in the treatment of occlusions in saphenous vein grafts, the coronary and carotid arteries, arteries arising from the aorta and branches thereof and in veins flowing to the heart or their tributaries and sub tributaries thereof.

19 Claims, 7 Drawing Sheets

U.S. PATENT DOCUMENTS

| | | |
|---|---|---|
| 7,163,504 B1 * | 1/2007 | Chiu et al. .................... 600/3 |
| 2004/0143240 A1 * | 7/2004 | Armstrong et al. ........... 604/528 |
| 2005/0245962 A1 * | 11/2005 | Adams et al. ................. 606/194 |
| 2006/0200075 A1 * | 9/2006 | Zadno-Azizi ............ 604/101.05 |
| 2007/0129733 A1 * | 6/2007 | Will et al. ..................... 606/108 |
| 2007/0250040 A1 * | 10/2007 | Provost et al. ................ 604/525 |

\* cited by examiner

ANGIOPLASTY BALLOON WITH THERAPEUTIC/ASPIRATION CHANNEL

CROSS-REFERENCE TO RELATED APPLICATIONS

This is a continuation of application Ser. No. 11/935,131 filed on Nov. 5, 2007, which claims priority to 60/857,082 filed Nov. 6, 2006 which are both incorporated herein by reference.

The present invention relates generally to angioplasty balloons and more particularly to angioplasty balloons with therapeutic delivery channels.

FIELD OF THE INVENTION

The present invention relates generally to angioplasty balloons and more particularly to angioplasty balloons with therapeutic delivery channels.

BACKGROUND OF THE RELATED ART

Atherosclerosis and cardiovascular disease are leading causes of mortality and morbidity worldwide. Each process can affect major and minor arterial vessels. Yet while arterial and venous thrombosis have numerous origins it is at the end organs where the effects of the thrombosis are most felt and where those effects result in clinical manifestation. Arterial thrombosis, for example, may manifest as sudden cardiac death, acute coronary syndromes (ACS), stroke, or peripheral embolization. Venous thrombosis may manifest as acute deep vein thrombosis (DVT), pulmonary embolism (PE), or paradoxical arterial embolization.

The underlying causes of these manifestations range from atherosclerosis due to plaque rupture or erosion (e.g., sudden death, ACS, etc), cardiac embolization from atrial fibrillation or left ventricular aneurysm (often secondary to coronary atherosclerosis), stasis and immobility (e.g., postoperative DVT), hypercoagulable state (activated protein C deficiency, malignancy), and a variety of rare disorders. Furthermore, thrombosis may complicate the performance of cardiovascular procedures or initiate malfunction of foreign devices implanted in the cardiovascular system valves, arterial stents, venous filters, bypass grafts, etc).

Given the deleterious impact of atherosclerosis, various interventions have been developed to reduce or remove blockages in blood vessels. One technique for treating stenosis or occlusion of a blood vessel is balloon angioplasty. A balloon catheter is inserted into the narrowed or blocked area, and the balloon is inflated to expand the constricted area. While commonly performed, this method is not without risk. Embolisms can occur during angioplasty when a blocking material dislodges and moves downstream further away of the balloon.

In coronary bypass surgery, a more costly and invasive form of intervention, a section of a vein, such as the saphenous vein taken from the kg, is used to form a connection between the aorta and the coronary artery distal to the obstruction. Over time, however, the saphenous vein graft may itself become diseased, stenosed, or occluded similar to the bypassed vessel. Atherosclerotic plaque in saphenous vein grafts, for example, tends to be more friable and less fibrocalcific than its counterpart in native coronary arteries.

Diffusely diseased saphenous vein grafts with friable atherosclerotic lesions and thrombi have been associated with iatrogenic distal embolic debris. As a result, balloon dilatation (angioplasty) of saphenous vein grafts is more likely to produce symptomatic embolization than dilatation of the coronary arteries. This is the case not only because of the difference in the plaque but also because saphenous vein grafts and their atheromatous plaques are generally larger than the coronary arteries to which they are anastomosed. Once the plaque and thrombi are dislodged from the vein, they can more easily move downstream, completely blocking another portion of the coronary artery and causing myocardial infarction. In fact, coronary embolisms from saphenous vein graft balloon angioplasty are more likely than in native coronary artery balloon angioplasty.

Because of these complications and high recurrence rates, old diffusely diseased saphenous vein grafts have been considered contraindications for standard angioplasty and atherectomy. These complications severely limit the options for minimally invasive treatment, yet the need for intervention remains.

Embolization is also harmful in patients undergoing interventions on the branches of the aortic arch (innominate, carotid, subclavian, vertebral) where the distal embolization may be associated with stroke and devastating neurological deficit. Similarly patients undergoing interventions to the kidney may have embolization and develop renal failure.

Given these limitations, considerable effort has been developed to limit embolization using emboli protection devices. Such devices are well known to those familiar with the art and comprise filters placed distal to the angioplasty site, occlusion devices placed distal to the site, or devices placed proximal to the site.

While these devices are effective at capturing detritus such as large emboli, they may allow small emboli to go across. Further, a reduction in flow across the filter is often noticed when the filter is overwhelmed. Further still, the embolic detritus can directly impact microcirculation and cause impairment of distal organ perfusion.

These complications can lead to myocardial infarction, arrhythmia or death during interventions on the coronary arteries or saphenous vein grafts. They can lead to stroke during interventions on the vessels supplying the brain, renal failure during renal interventions, pulmonary embolism during venous interventions, etc.

These complications are often treated either by administrating therapeutic agents to an angioplasty site or by aspirating columns of blood distal to the angioplasty site. Various agents have been studied for improving cell function and have been administered, in different studies, before or after angioplasty. These agents include beta blockers, adenosine, calcium channel blockers, nitroglycerine, nitroprusside, stem cells, growth factors and combinations thereof. However, given the size of the vessels involved, it is customary to perform angioplasty by removing the angioplasty device, introducing a different catheter, and then administering the therapeutic agent or aspiration. Often this necessitates premature removal of the guidewire, which can preclude access to distal vessels and thus is unpopular. Given the time delay involved with removing the angioplasty device and then inserting the therapeutic or aspiration mechanism, complications may result.

As a result, there is a need for a device that permits delivery of a therapeutic agent distal to the site of angioplasty in a rapid and easy fashion without requiring the removal of the angioplasty device.

SUMMARY OF THE INVENTION

The present application describes angioplasty balloons that have a channel for administering therapeutic agents to a vessel, for example, before, during or after balloon inflation. Also described are angioplasty balloon apparatuses for aspirating body fluids and emboli, thrombi, and other types of particles from a vessel distal to the angioplasty site. Various apparatuses are described, with some being particularly well suited for angioplasty within saphenous vein grafts, carotid arteries, coronary arteries, thrombotic AV fistulae and similar vessels.

An embodiment of the present invention is an angioplasty balloon catheter for administering therapeutic agents or aspirating body fluids, the angioplasty balloon catheter, comprising: an elongate flexible tubular body having a proximal end and a distal end, the body having an outer wall and an inner wall and capable of gaining access into a patient's coronary vessel or non-coronary vessel; a therapeutic lumen defined by the inner wall, the therapeutic lumen having a substantially uniformly circular cross-section from the proximal end to the distal end, the therapeutic lumen having a diameter between about 0.01 inches to about 0.09 inches; a therapeutic port at the proximal end of the tubular body and a therapeutic mouth at the distal end of the tubular body, the therapeutic port being in fluid communication with the therapeutic lumen and the therapeutic mouth; a guidewire lumen having a proximal end and a distal opening, wherein the guidewire lumen is adapted to receive a standard-size coronary guidewire therethrough, the guidewire lumen connected to the tubular body and adjacent the therapeutic lumen such that the therapeutic lumen and the guidewire lumen near the distal end form essentially a figure eight configuration, and such that said therapeutic lumen is unobstructed by said guidewire lumen, wherein the distal opening of the guidewire lumen is distal to the therapeutic mouth, the therapeutic mouth facing away from the guidewire lumen, whereby the guidewire lumen remains unobstructed during operation; and an inflation channel extending through the tubular body and capable of delivering inflation pressure to an angioplasty balloon.

Another embodiment of the present invention is a method of applying a therapeutic agent with an angioplasty balloon catheter apparatus, the method comprising: providing an elongate flexible tubular body having proximal end, a distal end, an outer wall, and an inner wall for insertion into a vessel; defining within the tubular body a therapeutic lumen defined by the inner wall, the therapeutic lumen having a substantially uniformly circular cross-section from the proximal end to the distal end, the therapeutic lumen having a diameter between about 0.01 inches to about 0.09 inches, the therapeutic lumen having a therapeutic port at the proximal end and a therapeutic mouth at the distal end, the therapeutic port being in fluid communication with the therapeutic lumen and the therapeutic mouth; providing a guidewire lumen adjacent the therapeutic lumen and having a proximal end and a distal opening, the guidewire lumen being adapted to receive a standard-size coronary guidewire therethrough, and positioning the guidewire lumen adjacent to the therapeutic lumen such that the therapeutic lumen and the guidewire lumen near the distal end form essentially a figure eight configuration, and positioning the guidewire lumen to extend distally from the therapeutic mouth; providing an inflation channel extending through the tubular body and capable of delivering inflation pressure to an angioplasty balloon of the catheter; and coupling a therapeutic source to the therapeutic port for establishing fluid communication with the therapeutic port for delivering a therapeutic agent to the therapeutic lumen.

Another embodiment of the present invention is a method of aspirating a body fluid with an angioplasty balloon catheter apparatus, the method comprising: providing an elongate flexible tubular body having a proximal end, a distal end, an outer wall, and an inner wall for insertion into a vessel; defining within the tubular body an aspiration lumen defined by the inner wall, the aspiration lumen having a substantially uniformly circular cross-section from the proximal end to the distal end, the aspiration lumen having a diameter between about 0.01 inches to about 0.09 inches, the aspiration lumen having an aspiration port at the proximal end and an aspiration mouth at the distal end, the aspiration port being in fluid communication with the aspiration lumen and the aspiration mouth; providing a guidewire lumen adjacent the aspiration lumen and having a proximal end and a distal opening, the guidewire lumen being adapted to receive a standard-size coronary guidewire therethrough, and positioning the guidewire lumen adjacent to the aspiration lumen such that the aspiration lumen and the guidewire lumen near the distal end form essentially a figure eight configuration, and positioning the guidewire lumen to extend distally from the aspiration mouth; providing an inflation channel extending through the tubular body and capable of delivering inflation pressure to an angioplasty balloon of the catheter; and coupling a source of negative pressure to the aspiration port for establishing fluid communication with the aspiration port and aspirating the body fluid through the aspiration lumen.

Another embodiment of the present invention is a method stent delivery with an angioplasty balloon catheter apparatus, the method comprising: providing an elongate flexible tubular body having a proximal end, a distal end, an outer wall, and an inner wall for insertion into a vessel; defining within the tubular body a first lumen defined by the inner wall, the first lumen having a port at the proximal end and a mouth at the distal end, the port being in fluid communication with the first lumen and the mouth; providing a guidewire lumen adjacent the first lumen and having a proximal end and a distal opening, the guidewire lumen being adapted to receive a standard-size coronary guidewire therethrough, and positioning the guidewire lumen adjacent to the first lumen such that the first lumen and the guidewire lumen near the distal end form essentially a figure eight configuration, and positioning the guidewire lumen to extend distally from the mouth; providing an inflation channel extending through the tubular body and capable of delivering inflation pressure to an angioplasty balloon of the catheter, the inflation channel having a non-inflated state and an inflated state; and positioning a stent on the angioplasty balloon, the stent being in a non-deployed position when the inflation channel is in a non-inflated state and the stent being in a deployed position when the inflation channel is in the inflated state; coupling a therapeutic source to the first port for delivering a therapeutic agent to the first lumen or coupling an aspiration source for aspirating body fluid through the first lumen; and inflating the inflation channel to place the stent in the deployed state.

The features, functions, and advantages can be achieved independently in various embodiments of the present invention or may be combined in yet other embodiments.

DESCRIPTION OF DETAILED EXAMPLES

Example angioplasty balloon catheter apparatuses capable of therapeutic delivery or aspiration are described. Generally, these apparatuses include structures for inserting and inflating angioplasty balloons, as well as mechanisms for delivering therapeutics or aspiration before, during or after balloon inflation or deflation. The balloon may be a monorail angioplasty balloon, for example, coupled with a therapeutic channel. A single catheter may provide an angioplasty balloon on a shaft, a guidewire channel that runs along the entire or partial length of the shaft, an inflation channel to inflate and deflate the balloon, and a therapeutic aspiration channel for administering a local therapeutic to the treated region or aspiring the region of blood, emboli, thrombi, etc.

The therapeutic or aspiration channel may be sized and shaped to deliver therapeutic agents and/or remove plaque, thrombi, emboli, and other types of detritus from blood vessels distal to the angioplasty site. The catheter apparatus may be adapted to be compactly utilized in even the smaller size blood vessels, such as branches of the coronary vessels or intracranial vessels. The catheter apparatus can also be adapted to provide efficient and speedy use in larger size vessels. This apparatus may be formed so as to be compatible with common therapy devices and may be designed for rapid evacuation and ease of use.

The catheter apparatuses may be provided in either over-the-wire or in single operator form. Radiopaque markers may be incorporated into the distal ends of the catheters to facilitate their positioning within the body. The catheters may be provided with varying flexibility along the length of the shaft, such that they are soft and flexible enough to be navigated through the vasculature of a patient without causing damage, but are stiff enough to sustain the axial push required to position the catheter properly and to sustain the aspiration pressures.

Figure 1:
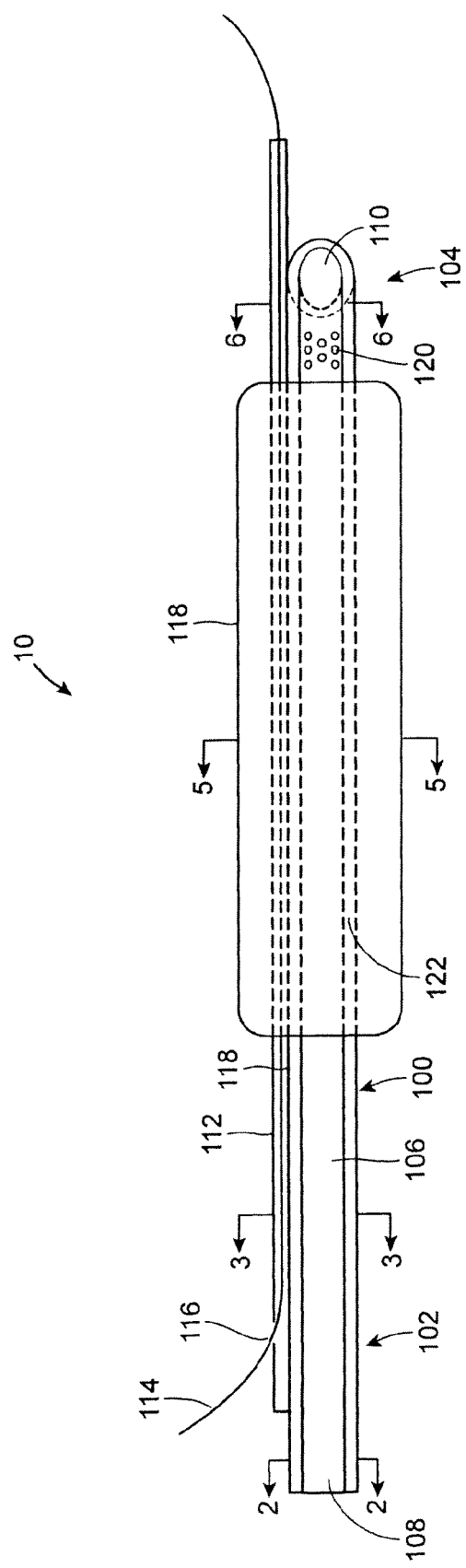
FIG. 1 illustrates an example angioplasty balloon catheter apparatus having a therapeutic channel in accordance with an example.

FIG. 1 illustrates an example catheter apparatus 10 that comprises an elongate flexible tubular body 100 having a proximal end 102 and a distal end 104. The catheter body or shaft may incorporate a reinforcement (not shown) such as a metallic braid or coil or a polymer coil to provide strength and flexibility to the device. A therapeutic lumen (channel) 106 extends the length of the tubular body 100 and has a therapeutic port 108 at the proximal end 102 in fluid communication with the therapeutic lumen 106, such that therapeutic agents can be delivered or aspiration pressure can be provided through the port and lumen.

The distal end 104 of the tubular body 100 may be formed of a more flexible material than that used to form the rest of the catheter shaft.

The therapeutic lumen 106 may be defined by an inner wall of the tubular body 100 and is preferably substantially uniform and circular in cross-section from the proximal end 102 to the distal end 104, although this need not be the case. The therapeutic lumen 106 may have a diameter of between approximately 0.01 inches and approximately 0.09 inches, in an example. The lumen 106 may have a mouth 110 at the distal end 104 opposite the port 108 for distally communicating the therapeutic or collecting detritus or blood during aspiration.

The reinforcement for the tubular body 100 can be formed from a variety of materials, including polymers, stainless steel, silver or gold plated stainless steel, platinum, nitinol, or a combination thereof. The distal end 104 of the catheter body 100 is preferably more flexible than the proximal end 102. In addition to using different materials for the catheter, flexibility may be achieved by providing a braid or coil density at the distal end which is greater or lesser than the braid or coil density at the proximal end.

The angioplasty catheter also includes a second lumen 112, adjacent the therapeutic lumen 106 (in cross-section) and adapted to receive a guidewire 114. This guidewire lumen 112 may extend substantially the entire length of the tubular body 100, or (as shown in FIG. 1) may extend distally from the end 104. For example, the guidewire lumen 112 may extend beyond the distal end 104 by approximately 40 mm, approximately 20 mm, or smaller distances as desired. The second lumen 112 may contain a slit 116 through a side wall to allow insertion and removal of the guidewire. In an example, the second lumen 112 has an inner diameter of approximately 0.020 inches to receive a 0.014 inch diameter guidewire. More generally, in some examples, the lumen 112 may have any inner diameter over a range of approximately 0.008 inches to approximately 0.038 inches.

In some examples, the maximum profile of the apparatus 10 pre balloon inflation may be 1.8 mm at the proximal end 102 and 0.9 mm beyond the distal end to the channel. The guidewire lumen 112 may be formed of a shaft length of 135 cm, for example, with the guidewire exiting at 30 cm beyond the distal end 104.

The mouth 110 of the therapeutic lumen 106 and the mouth of the guidewire lumen 112 may form essentially a figure eight shape in end view. In some examples, the guidewire lumen may be within the therapeutic channel, still forming an essentially figure eight configuration. In some examples, the mouth 110 may form an oblique opening that faces away from the guidewire lumen 112, such as in FIG. 1A. In other examples, the mouth 110 may form a transverse opening (such as in FIG. 1B), may face toward the guidewire lumen 112 (such as in FIG. 1C), or may have multiple openings. The proximal end of the guidewire lumen 112 may itself form an oblique opening that faces away from the tubular body 100, towards the tubular body 100, transverse to the tubular body 100 or another orientation.

The angioplasty catheter of FIG. 1 may also include a third, inflation lumen, or channel, (not labeled in FIG. 1) inflating or deflating an angioplasty balloon 118. Example inflation channels are described with reference to FIGS. 2-6B below. The balloon 118 may be an approximately 5.5 or 6 mm diameter balloon approximately 20 mm in length for large vessels or an approximately 2.5 or 3 mm diameter balloon approximately 12 to 15 mm in length for moderate sized vessels, for example. The balloon 118 is not limited to these examples, of course.

The distal tip 104 of the tubular body 100 can have at least one or more side ports 120 (in addition to or in place of the mouth opening 110) to deliver therapeutic agent or to facilitate aspiration. In some examples, the therapeutic channel 106 ends proximal to the end 104 of the balloon catheter so that drugs may be applied at or proximal to the angioplasty site, which may be useful for reducing local inflammation. FIG. 1D shows an example configuration of a portion of the tubular body 100 where the therapeutic lumen 106 is terminated internally and proximal to the balloon 118 by a lumen stop 117 extending across the entire cross-section of the lumen 106 in the illustrated example to fully prevent additional downstream flow. Therapeutic within the lumen 106 is delivered proximal to the balloon 118 through delivery channels 119 formed in the side of the tubular body 100. Although only certain channels 119 are shown it will be understood that more or fewer channels may be provided and at different locations along with tubular body 100.

Figure 1A:
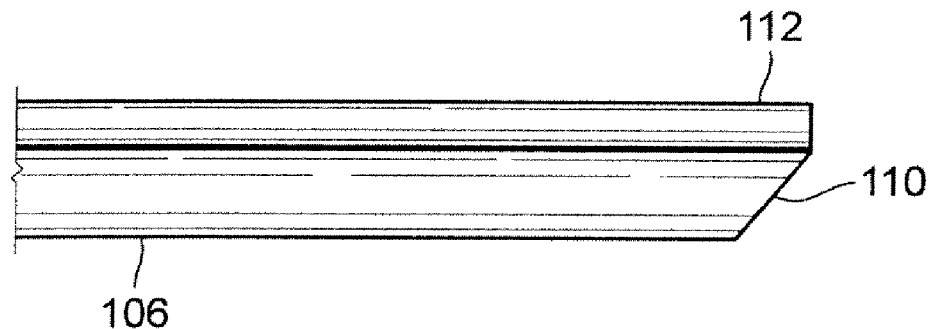
FIGS. 1A-1C illustrate various example orientations for mouth opening on a therapeutic channel in relation to a guidewire channel.
Figure 1B:
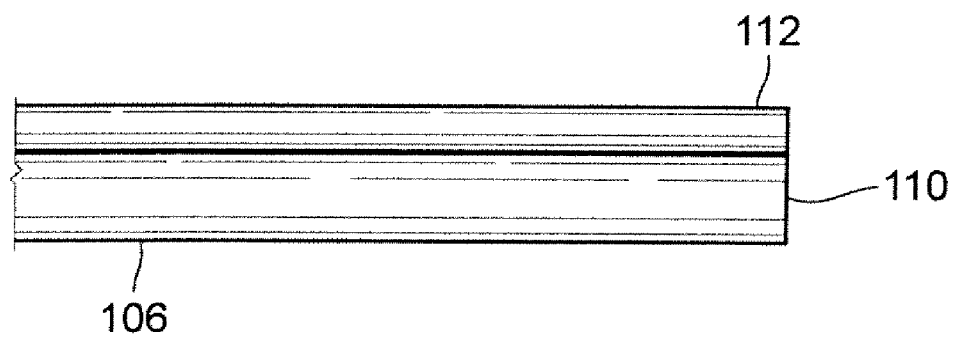
Figure 1C:
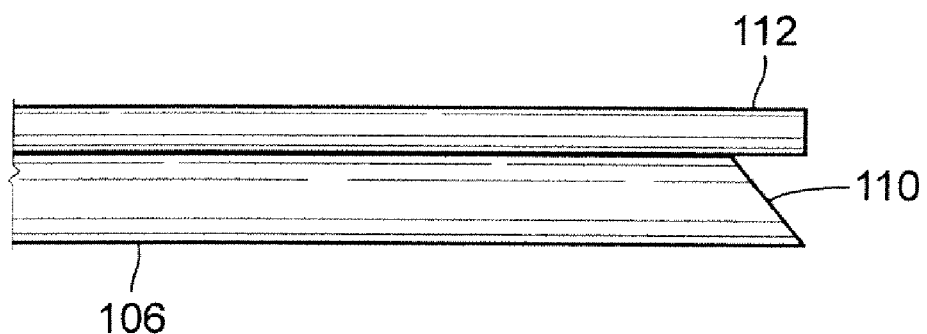
Figure 1D:
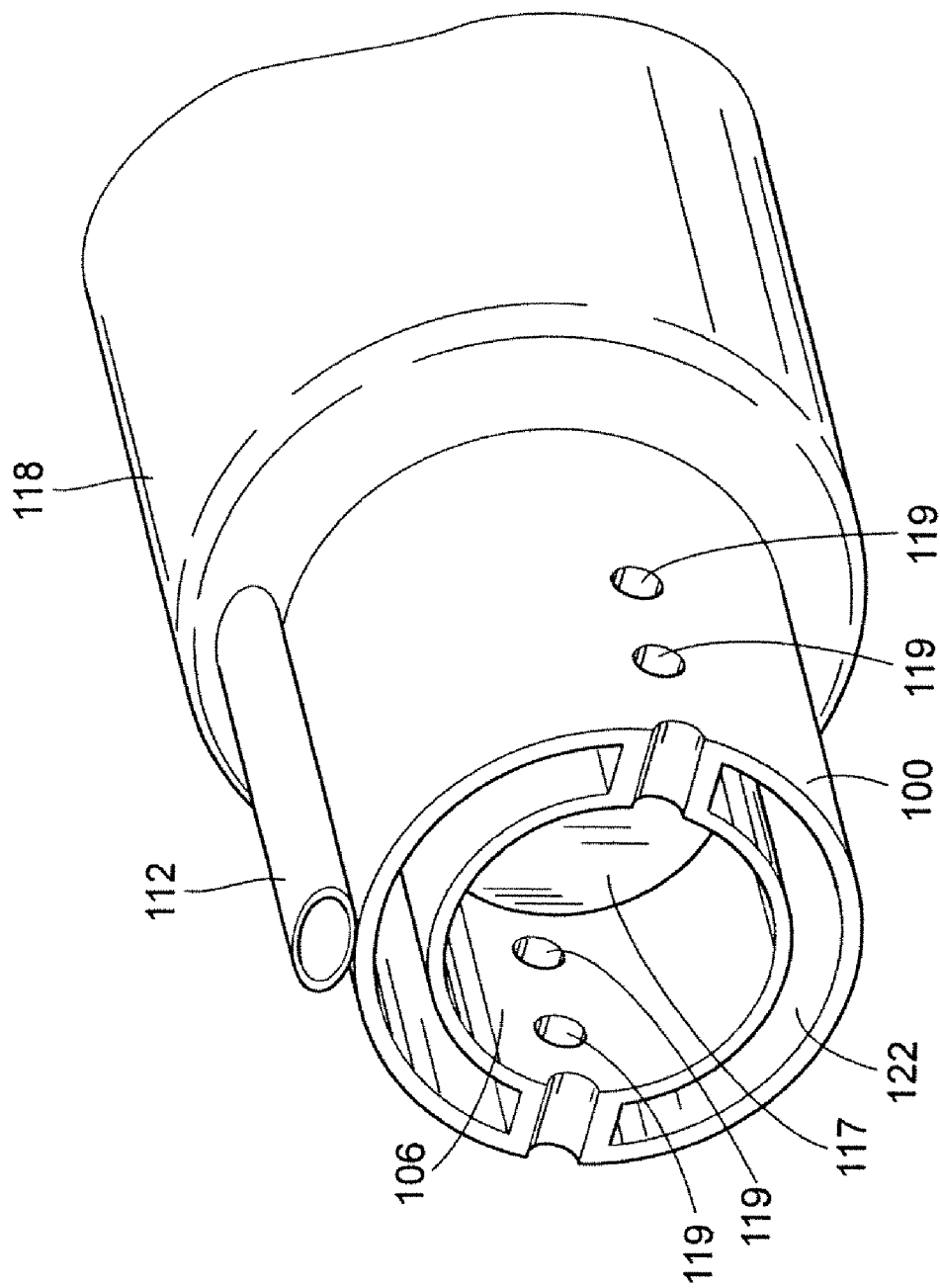
FIG. 1D illustrates a portion of a tubular body in which therapeutics may be delivered proximal to a balloon.

The distal tip 104 can be tapered, blunt, or angled to create an oblique mouth opening, as demonstrated in the examples of FIGS. 1A-1C. The catheter body 100 may comprise or be connected to a valve in fluid communication with the lumen 106, to control the application of aspiration pressure at the distal end of the device, in some examples. The aspiration catheter in some examples may also incorporate various coatings, such as hydrophilic or hydrophobic coatings, antithrombogenic coatings, or a combination thereof.

Further, in some examples, the therapeutic channel can be constructed in a fashion that permits capture of the filter device used downstream of the apparatus 10. For example, the apparatus 10 may be used with an emboli protection device, such as a distal filter, distal occlusion device, or proximal occlusion device. This could entail the therapeutic port having a single transverse opening ending parallel to the guidewire channel.

Figure 2:
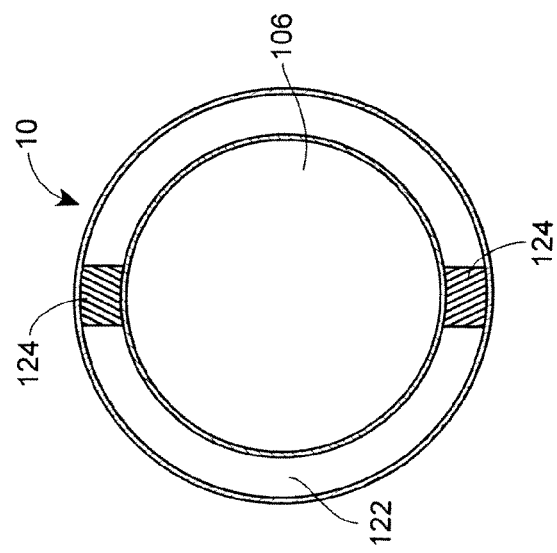
FIG. 2 illustrates a cross-sectional view (taken at lines 2-2) of a mid portion of the angioplasty balloon catheter of FIG. 1.

FIG. 2 illustrates a cross-section of the catheter 10 (taken along lines 2-2 in FIG. 1) and showing the therapeutic channel 106 and an inflation channel 122 concentric therewith. The inflation channel 122 surrounds the channel 106 and likewise may be uniformly circular or C-shaped in cross-section.

Figure 3:
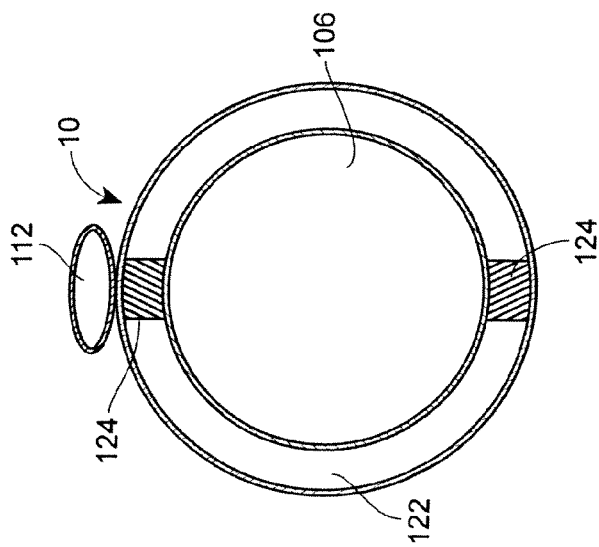
FIG. 3 illustrates a cross-sectional view (taken at lines 3-3) of a portion of the angioplasty balloon catheter of FIG. 1 in an example.

FIG. 3 illustrates a cross-section of the catheter 10 (taken along lines 3-3 in FIG. 1) and showing the therapeutic channel 106, the inflation channel 122, and the guidewire lumen 112 exterior to the therapeutic channel 106. The guidewire lumen 112 has an elliptical or oblong profile in the illustrated example, such that a vertical extent (along a radial direction of the channel 106) is shorter than a lateral extent to reduce the overall profile of the catheter apparatus 10. The guidewire lumen 112 is shown formed exterior to a channel attachment seem 124. The inflation channel 122 surrounds the channel 106 and likewise may be uniformly circular or C-shaped in cross-section.

Figure 4:
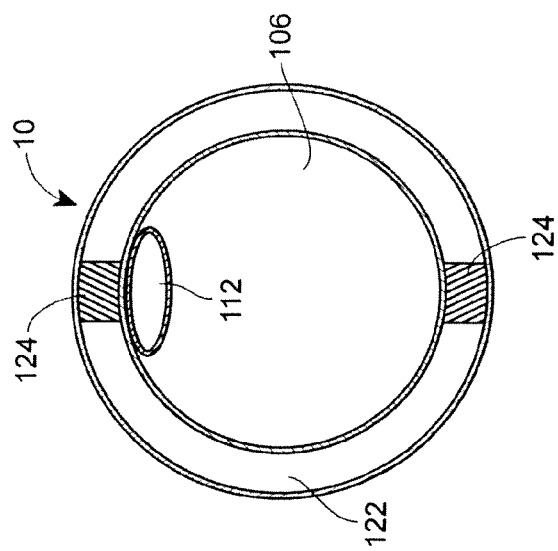
FIG. 4 illustrates a cross-sectional view of a portion of the angioplasty balloon catheter of FIG. 1 in another example from that of FIG. 3.

FIG. 4 illustrates an alternative embodiment similar to that of FIG. 3 but with the guidewire lumen 112, in an essentially figure eight configuration but) formed interior to the therapeutic channel 106 at an interior surface of the seem 124.

Figure 5B:
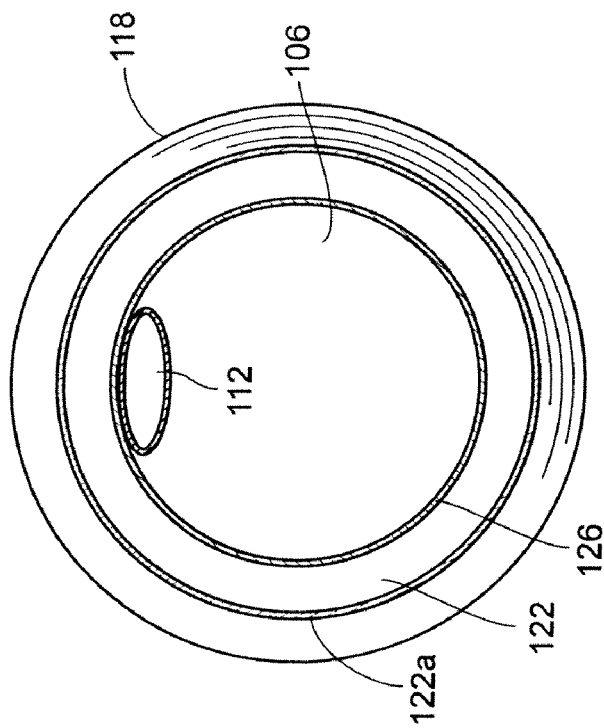
FIGS. 5A and 5B illustrate cross-sectional views (taken at lines 5-5) of portions of the angioplasty balloon catheter of FIG. 1 in accordance with different examples, respectively.
Figure 5A:
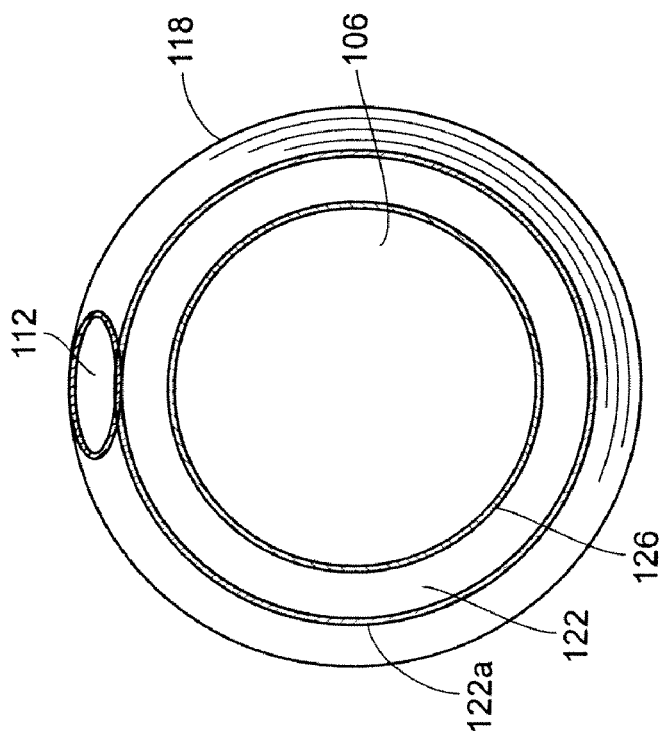

FIG. 5A illustrates a cross-section (at lines 5-5 of FIG. 1) showing an exterior formed guidewire lumen 112, the inflation channel 122, the therapeutic channel 106, and the angioplasty balloon 118. The therapeutic channel 106 at least at this portion of the tubular body 110 is protected against inward deformation pressures (from the inflation channel 122) by a protective ring 126. The ring 126 may represent a different, more resilient material than that remainder of the therapeutic channel 106, or the ring 126 may be a physical harrier formed to prevent all or substantially all inward de of the therapeutic channel 106.

The inflation channel 122 may be supplied with a fluid urce for inflating, the balloon 118, e.g., via coupling a fluid source into an opening (not shown) at a proximal of the tubular body 100. Alternatively to or in addition to forming the ring 126 of a resilient material, inflation can be achieved by forming that portion 122a of the inflation channel outer wall coinciding with the balloon 118 with a less resilient, easier to inflate material. Alternatively still, that portion 122a of the inflation channel outer wall coinciding with the balloon 118 may be porous to allow fluid injected into the inflation channel 122 to fill the balloon 118. It will be understood that the present application is not limited in regards to inflation technique.

FIG. 5B illustrates another embodiment like that of FIG. 5A, but with the guidewire lumen 112 interior to the therapeutic channel 106.

Figure 6B:
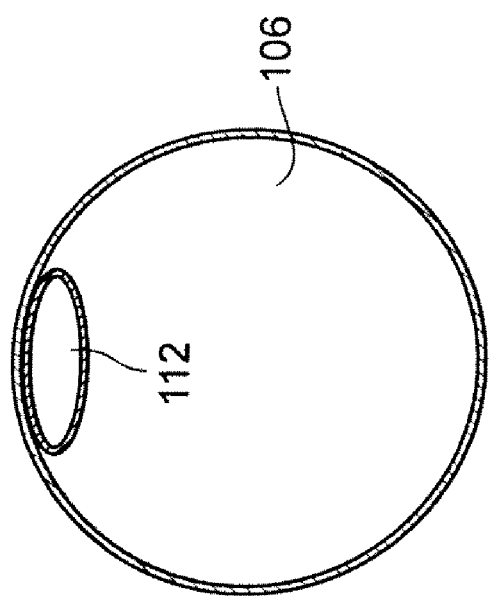
FIGS. 6A and 6B illustrates cross-sectional views (taken at lines 6-6) of a distal portion the angioplasty balloon catheter of FIG. 1 in accordance with different examples, respectively.
Figure 6A:
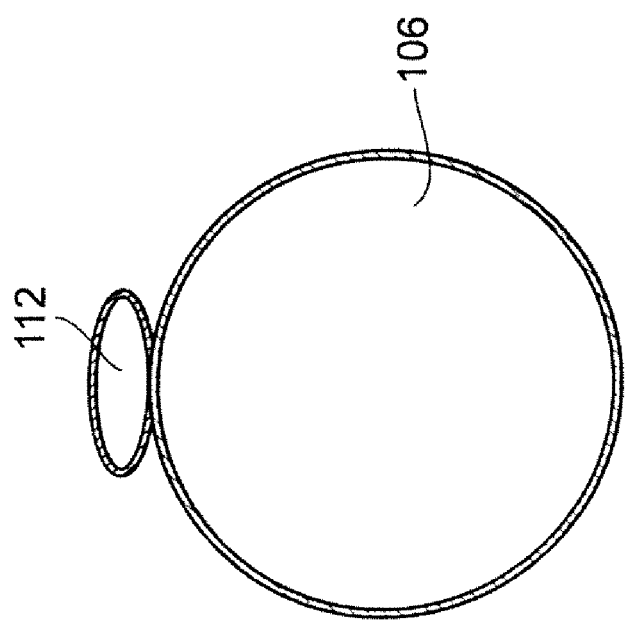

FIG. 6A illustrates a cross-section (at lines 6-6 of FIG. 1) of the catheter 10 at the distal end 104 of the tubular body 100. As illustrated the guidewire lumen 112 and the therapeutic channel 106 form an essentially figure eight configuration. FIG. 6B illustrates a similar cross-section but with the guidewire lumen 112 shown interior to the therapeutic channel 106, still forming an essentially figure eight configuration.

Described are catheters that may be used for fast and efficient aspiration of the working area surrounding the occlusion in a blood vessel of for fast and efficient therapeutic delivery. The catheters may be utilized in a wide range of vessel diameters, including extremely small ones. The catheters are easy to use and can quickly and efficiently evacuate occlusions and debris, allowing the physician to restore normal blood flow in these vessels in a very short period of time.

The catheters may be of combined use as well, providing therapeutics during some periods and aspiration during others. And either may be performed before, during, or after an angioplasty balloon inflation or deflation.

The assemblies described herein may be formed through techniques such as blow molding or heat shrinking a thermoplastic film or tubing. Extrusion techniques may be used as well. Suitable materials will be known and include, by way of example, PET, polyesters, nylon, PVC, and polyethylene.

Although shown in a uniform cross-section, the lumens described may be tapered toward the distal end and/or toward the proximal end as desired. Further while some inner lumen walls are illustrated as continuous curves (e.g., circular in cross-section), am of the lumen walls may be elliptical in cross-section or take on other shapes, including having planar walls or wall portions. The geometry of the lumen may vary. Further still the lumens may extend the entire linear length of the tubular body or at least some of the lumens (e.g., the guidewire and inflation lumens) may be helically formed to coil around a central axis and body of the therapeutic lumen.

Persons of ordinary skill in the art will appreciate that the disclosed teachings may be used in any number of implementations and any number of applications including coronary arteries, carotid arteries, renal arteries and saphenous vein graft applications mentioned above. The apparatuses and techniques described herein are not limited to a particular application. Some further examples are provided below, and yet other examples will become apparent by referencing the claims.

Example Cardiac Applications

The techniques described could be used in a variety of applications. For example, in treatment for cardiac conditions, such as acute MI and SVG interventions, the catheter would permit aspiration after and during angioplasty and thus limit embolization. The catheter would permit delivery of pharmaceutical agents (such as beta blockers, adenosine, calcium channel blockers, nitroglycerine, nitroprusside, stem cells, growth factors and combinations there the distal bed without having to change catheters or introduce new devices in the artery. The catheter could deliver other agents including a naturally occurring substance, an embryonic cell, a fetal cell, a transgenic cell, an adult human cell, a modified cell, a modified cellular agent, a sub-cellular structure, an agent capable of modifying cellular function or structure, or a combination thereof. The catheter could perform aspiration thrombectomy prior to, during, and following angioplasty to remove embolic burden and thus improve distal perfusion. These applications could be combined (e.g., angioplasty and aspiration) to permit more rapid establishment of flow to the distal bed.

Example Carotid Applications

In non-cardiac conditions, the techniques can provide carotid interventions. For example, the catheter may be used as the standard for administering the post dilation balloon. This would allow aspiration to be performed on every patient after post-dilation and reduce the risk of emboli overwhelming the filter. In patients with occlusion devices, the techniques could be the preferred post dilation balloon administering techniques, since immediate aspiration could be achieved. This would reduce the time the vessel is occluded.

Recent data suggest that slow flow occurs in approximately 10% of the cases undergoing protected carotid artery stenting. This phenomenon commonly occurs following post dilation of a recently deployed carotid stent and is believed to be secondary to release of plaque debris that overwhelm the filter. Furthermore, release of plaque components is believed to release vasoactive substances that secondarily lead to platelet activation and aggregation and microthrombi formation. Some of these humoral mediators are believed to be responsible for the global cerebral dysfunction that can follow carotid stenting. Given that the patients with slow flow are at very high risk of stroke after the filter is removed, it is customary to introduce an aspiration catheter or a diagnostic catheter such a multipurpose catheter to aspirate the column of blood in the internal carotid artery up to the filter. This strategy is believed to limit the hazard of embolization that may follow removal of the filter.

A potential concern with this strategy is that the longer slow flow persists, the greater the risk of further thrombosis. Thus the operator has to balance the need for efficient removal of the blood column with suspended plaque debris, with the need to quickly remove the filter.

The current techniques may thus be used as the post stenting angioplasty balloon insertion device. Thus, the balloon may be introduced after the carotid stem is deployed, and aspiration is performed while the balloon is deflated. Any suspended debris is automatically removed. As a result, no time is wasted in removing the device, checking flow and then re-introducing another device It is foreseeable that the same benefits may apply in other non-coronary beds where embolization may be an issue and thus the catheter device techniques may be used in renal interventions or as a stent delivery vehicle for large arteries such as the subclavian, common carotid, or innominate arteries. Currently these vessels are stented with limited protection since they give rise to multiple branches. However, the present techniques would permit creation of reversal of flow while the stent is being deployed and thus limit distal embolization.

Figure 7:
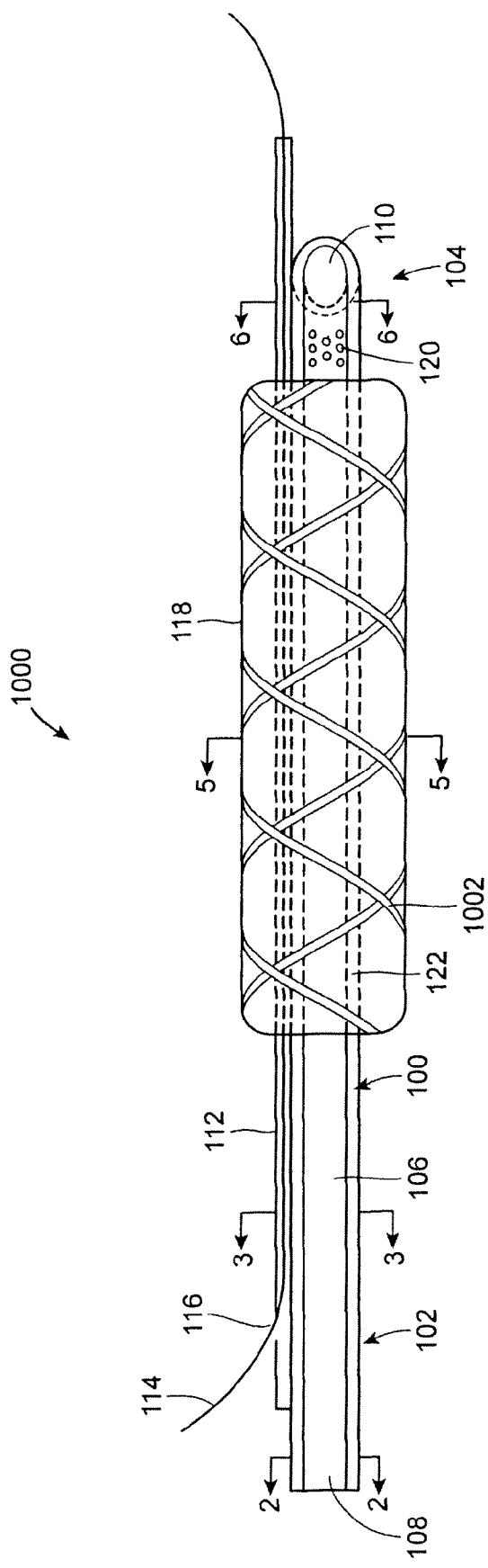
FIG. 7 illustrates an example angioplasty balloon catheter and stent apparatus having a therapeutic channel in accordance with an example.

FIG. 7 illustrates an example stent apparatus 1000 similar to apparatus 10 and therefore bearing like reference numbers. The apparatus 1000 includes a deployable stent 1002 shown in a non-deployed position surround the balloon 118. The stent 1002 is dilated by the inflation of the balloon 118, in the illustrated example. It will be appreciated that in other examples a self-expandable stent may be used instead with the balloon 118, if there is one, allowing the balloon 118 to be used for angioplasty clearance of detritus only.

In addition to the example of FIG. 7, the angioplasty catheter may be used as a delivery catheter for other in-vessel devices such as in a laser or mechanical atherectomy catheter or ultrasonic or laser plaque modifying/ablation device. Such devices may be combined with the catheters described herein for operation within the vessel and before, during, or after therapeutic delivery or aspiration.

Although certain apparatus constructed in accordance with the teachings of the invention have been described herein, the scope of coverage of this patent is not limited thereto. On the contrary, this patent covers all embodiments of the teachings of the invention fairly falling within the scope of the appended claims either literally or under the doctrine of equivalents.

What is claimed is:

1. A method of applying a therapeutic agent with an angioplasty balloon catheter apparatus, the method comprising:
    providing an elongate flexible tubular body having a proximal end, a distal end, an outer wall, and an inner wall for insertion into a vessel;
    defining within the tubular body a therapeutic lumen defined by the inner wall, the therapeutic lumen having a substantially uniformly circular cross-section from the proximal end to the distal end, the therapeutic lumen having a diameter between about 0.01 inches to about 0.09 inches, the therapeutic lumen having a therapeutic port at the proximal end and a therapeutic mouth at the distal end, the therapeutic port being in fluid communication with the therapeutic lumen and the therapeutic mouth;
    providing a guidewire lumen adjacent the therapeutic lumen and having a proximal end and a distal opening, the guidewire lumen being adapted to receive a standard-size coronary guidewire therethrough, and positioning the guidewire lumen adjacent to the therapeutic lumen such that the therapeutic lumen and the guidewire lumen near the distal end form essentially a figure eight configuration, wherein the guidewire lumen is provided on the interior of the tubular body, and positioning the guidewire lumen to extend distally from the therapeutic mouth;
    providing an inflation channel extending through the tubular body and capable of delivering inflation pressure to an angioplasty balloon of the catheter; and
    coupling a therapeutic source to the therapeutic port for establishing fluid communication with the therapeutic port for delivering a therapeutic agent to the therapeutic lumen.

2. The method of claim 1, comprising delivering the therapeutic agent before balloon inflation.

3. The method of claim 1, comprising delivering the therapeutic agent after balloon inflation.

4. The method of claim 1, comprising delivering the therapeutic agent during balloon inflation.

5. The method of claim 1, wherein the therapeutic agent is a pharmaceutical agent, a naturally occurring substance, a stem cell, an embryonic cell, a fetal cell, a transgenic cell, an adult human cell, a modified cell, a modified cellular agent, a sub-cellular structure, an agent capable of modifying cellular function or structure, or a combination thereof.

6. The method of claim 1, wherein the therapeutic port is used to aspirate the body fluids distal to the site of angioplasty.

7. The method of claim 1 where the therapeutic port is used to aspirate plaque debris suspended in a column of blood distal to the site of angioplasty.

8. The method of claim 1, further comprising inserting the tubular body into the vessel already protected by a previously placed emboli protection device.

9. The method of claim 8, wherein the emboli protection device is a distal filter.

10. The method of claim 8, wherein the emboli protection device is a distal occlusion device.

11. The method of claim 8, wherein the emboli protection device is a proximal occlusion device.

12. The method of claim 1, further comprising administering the therapeutic agent before balloon inflation.

13. The method of claim 1, further comprising administering the therapeutic agent during balloon inflation.

14. The method of claim 1, further comprising administering the therapeutic agent after balloon inflation.

15. The method of claim 1, further comprising aspirating body fluid before, during or after balloon inflation.

16. A method stent delivery with an angioplasty balloon catheter apparatus, the method comprising:
   providing an elongate flexible tubular body having a proximal end, a distal end, an outer wall, and an inner wall for insertion into a vessel;
   defining within the tubular body a first lumen defined by the inner wall, the first lumen having a port at the proximal end and a mouth at the distal end, the port being in fluid communication with the first lumen and the mouth;
   providing a guidewire lumen adjacent the first lumen and having a proximal end and a distal opening, the guidewire lumen being adapted to receive a standard-size coronary guidewire therethrough, and positioning the guidewire lumen adjacent to the first lumen such that the first lumen and the guidewire lumen near the distal end form essentially a figure eight configuration, wherein the guidewire lumen is provided on the interior of the tubular body, and positioning the guidewire lumen to extend distally from the mouth;
   providing an inflation channel extending through the tubular body and capable of delivering inflation pressure to an angioplasty balloon of the catheter, the inflation channel having a non-inflated state and an inflated state; and
   positioning a stent on the angioplasty balloon, the stent being in a non-deployed position when the inflation channel is in a non-inflated state and the stent being in a deployed position when the inflation channel is in the inflated state;
   coupling a therapeutic source to the first port for delivering a therapeutic agent to the first lumen or coupling an aspiration source for aspirating body fluid through the first lumen; and
   inflating the inflation channel to place the stent in the deployed state.

17. The method of claim 16, wherein coupling the therapeutic source to the first port for delivering the therapeutic agent to the first lumen or coupling the aspiration source for aspirating the body fluid through the first lumen occurs before stent deployment.

18. The method of claim 16, wherein coupling the therapeutic source to the first port for delivering the therapeutic agent to the first lumen or coupling the aspiration source for aspirating the body fluid through the first lumen occurs after stent deployment.

19. The method of claim 16, wherein coupling the therapeutic source to the first port for delivering the therapeutic agent to the first lumen or coupling the aspiration source for aspirating the body fluid through the first lumen occurs during stent deployment.

* * * * *